(12) United States Patent
Ritoniemi

(10) Patent No.: US 9,532,015 B2
(45) Date of Patent: Dec. 27, 2016

(54) SYNCHRONIZATION OF IMAGING

(71) Applicant: Procemex Oy, Jyväskylä (FI)

(72) Inventor: Jari Ritoniemi, Pirkkala (FI)

(73) Assignee: Procemex OY, Jyväskylä (FI)

( * ) Notice: Subject to any disclaimer, the term of this patent is extended or adjusted under 35 U.S.C. 154(b) by 0 days.

(21) Appl. No.: 14/902,852

(22) PCT Filed: Jul. 7, 2014

(86) PCT No.: PCT/FI2014/050564
§ 371 (c)(1),
(2) Date: Jan. 5, 2016

(87) PCT Pub. No.: WO2015/001196
PCT Pub. Date: Jan. 8, 2015

(65) Prior Publication Data
US 2016/0142682 A1     May 19, 2016

(30) Foreign Application Priority Data
Jul. 5, 2013 (FI) .................................... 20135749

(51) Int. Cl.
*H04N 9/47* (2006.01)
*H04N 7/18* (2006.01)
(Continued)

(52) U.S. Cl.
CPC ............ *H04N 7/183* (2013.01); *D21G 9/0009* (2013.01); *G01N 21/89* (2013.01); *G01N 33/346* (2013.01);
(Continued)

(58) Field of Classification Search
None
See application file for complete search history.

(56) References Cited

U.S. PATENT DOCUMENTS 5,935,285 A * 8/1999 Lucas ..................... C03B 9/41
198/339.1
2002/0166970 A1 * 11/2002 Komulainen ........ D21G 9/0027
250/340

(Continued)

FOREIGN PATENT DOCUMENTS

EP      0979995        2/2000
EP      1258722       11/2001
(Continued)

OTHER PUBLICATIONS

Kumar A: Computer-vision-based fabric defect detection: a survey'. IEEE Trans. on Industrial electronics, vol. 55. No. 1. Jan. 2008, pp. 348-363.
(Continued)

*Primary Examiner* — Frederick Bailey
*Assistant Examiner* — Talha M Nawaz
(74) *Attorney, Agent, or Firm* — Berggren, Inc.

(57) ABSTRACT

The invention relates to a method, the method comprises exposing an image frame of an object to be monitored by an area image sensor, transmitting a part of the exposed image frame to an image data processing device, analyzing the part and if the part is detected to comprise a predefined event, said image data processing device is arranged to transmit a trigger signal for triggering said area image sensor so that said area image sensor transmits a bigger part of at least one further image frame to said image data processing device for further analysis, and if not the area image sensor continues to expose at least one further image frame and to transmit a part of said at least one exposed further image frame. The invention further relates to a machine vision system for performing the method and a computer program product comprising instructions to perform the method.

19 Claims, 4 Drawing Sheets

(51) Int. Cl.
*G01N 21/89* (2006.01)
*D21G 9/00* (2006.01)
*G01N 33/34* (2006.01)
*G06T 7/00* (2006.01)
*H04N 5/235* (2006.01)

(52) U.S. Cl.
CPC ............. *G06T 7/001* (2013.01); *H04N 5/2353* (2013.01); *G06T 2207/30124* (2013.01)

(56) References Cited

U.S. PATENT DOCUMENTS

| | | | |
|---|---|---|---|
| 2005/0117017 A1 | 6/2005 | Baer | |
| 2005/0232478 A1* | 10/2005 | Onishi | G06T 7/0004 382/149 |
| 2007/0013954 A1* | 1/2007 | Soeda | H04N 1/401 358/3.26 |
| 2007/0211242 A1* | 9/2007 | Okabe | G01N 21/8806 356/237.2 |
| 2008/0001104 A1* | 1/2008 | Voigt | G01N 21/8851 250/559.46 |
| 2008/0292178 A1* | 11/2008 | Sones | G01N 21/909 382/152 |
| 2009/0214102 A1* | 8/2009 | Maeda | G01N 21/95607 382/144 |
| 2010/0150413 A1* | 6/2010 | Futamura | G06T 7/0012 382/128 |
| 2010/0163732 A1* | 7/2010 | Louban | G01N 25/72 250/341.6 |
| 2011/0123119 A1* | 5/2011 | Yamanaka | G01N 29/069 382/190 |
| 2011/0141269 A1 | 6/2011 | Varga | |
| 2011/0222754 A1* | 9/2011 | Zhao | G06T 7/0004 382/141 |
| 2012/0133763 A1 | 5/2012 | Schramboeck | |
| 2012/0293623 A1* | 11/2012 | Nygaard | G06T 7/0004 348/46 |
| 2013/0002283 A1* | 1/2013 | Celi | G01R 31/311 324/754.23 |
| 2013/0242084 A1* | 9/2013 | Inoue | G06T 7/0004 348/126 |
| 2013/0244142 A1* | 9/2013 | Yamane | G01N 21/956 430/5 |
| 2014/0210982 A1* | 7/2014 | Zuo | G06T 7/001 348/80 |

FOREIGN PATENT DOCUMENTS

| | | |
|---|---|---|
| EP | 1431456 | 6/2004 |
| EP | 1630550 | 3/2006 |
| WO | 0045156 | 8/2000 |

OTHER PUBLICATIONS

Finnish Patent and Registration Office—Office Action for Application FI20135795—dated on Nov. 27, 2014.
Finnish Patent and Registration Office—Office Action for Application FI 20135749—dated on Mar. 4, 2014.
Stojanovic R.et al. An approach for automated inspection of wood boards. IEE Int. Conf. on image processing ICIP 2001. Tessaloniki Greece 7-10/10 2001 pp. 798-801.
International Preliminary Report of Patentability for PCT/FI2014/050564 dated on May 29, 2015.

* cited by examiner

SYNCHRONIZATION OF IMAGING

PRIORITY

This application is a national application of PCT application PCT/FI2014/050564, filed on Jul. 7, 2014 and claiming priority of Finnish national application number FI20135749 filed on Jul. 5, 2013, the contents of both of which are incorporated herein by reference.

FIELD OF THE INVENTION

The present invention relates to a method for imaging of continuous manufacturing processes, in which method an area-scan camera is used for imaging of an object to be monitored.

The invention also relates to a system and a computer program product causing an apparatus to carry out the method.

BACKGROUND OF THE INVENTION

In continuous manufacturing processes, there are materials or products constantly running through the machine. In such processes, for example, in paper machines, the product must be monitored in order to detect possible deviations, and to obtain a final product of high quality, for example, by machine vision systems such as camera systems comprising a plurality of area-scan (array) cameras. With an area-scan camera, a matrix of pixels provides an image of the monitored target. As the monitored target moves past the area-scan camera system, images of it are exposed by an area image sensor of the camera and transferred to a processing unit for analysis.

The monitored process may contain events that need to be captured completely within a single image. The capturing of these events is often triggered by an external trigger signal received, for example, from a photoelectric cell, automatic logic, or a pulse sensor.

SUMMARY

The present invention relates to a method for a computing device, for example, an image data processing device of a machine vision system. An area image sensor of the machine vision system exposes an image frame of an object to be monitored without external triggering. A part of the image frame may be transferred to the image data processing device for analysing. When the image data processing device detects a predefined event in that part of the image frame, the configuration of the machine vision system is changed so that a bigger part of at least one further image frame is transferred from the area image sensor to a memory of the image data processing device for further analysis.

Various aspects of the invention include a method for a computing device of a machine vision system, a machine vision system and a computer program product comprising instructions to perform the method.

According to a first aspect of the invention, there is provided a method for exposing an image frame of an object to be monitored by an area image sensor, transmitting a part of said exposed image frame to an image data processing device, and analysing the received part of said image frame by said image data processing device, and if said received part of said image frame is detected to comprise at least one predefined event, said image data processing device is arranged to transmit a trigger signal for triggering said area image sensor so that said area image sensor transmits a bigger part of at least one further image frame to said image data processing device for further analysis, otherwise said received part of said image frame is not detected to comprise a predefined event, said area image sensor continues to expose at least one further image frame and to transmit a part of said at least one further image frame.

According to an embodiment, said part of the image frame comprises multiple separate sections of said image frame. According to an embodiment, said bigger part of the image frame comprises multiple separate sections of said image frame. According to an embodiment, said bigger part of said image frame is the whole image frame. According to an embodiment, said received part of said image frame determines the size and position of said bigger part of said image frame, or a number of image frames of which a bigger part is transmitted. According to an embodiment, the method further comprises exposing at least one further image frame and transmitting part of said at least one further image frame to said image data processing device after said bigger part of at least one further image frame is transmitted to said image data processing device for further analysis. According to an embodiment, said area image sensor is exposing image frames and transmitting parts of image frames without an external trigger signal.

According to an embodiment, said object to be monitored is a paper or cardboard web. According to an embodiment, said object to be monitored is a roll of a printing machine.

According to a second aspect of the invention, there is provided a machine vision system for an object to be monitored comprising an area image sensor and an image data processing device, wherein said area image sensor is arranged to expose an image frame of a moving object and to transmit a part of the exposed image frame to said image data processing device for analysing; and wherein said image data processing device is arranged to transmit a trigger signal for triggering said area image sensor so that said area image sensor transmits a bigger part of at least one further image frame to said image data processing device for further analysis if the received part of said image frame is detected to comprise at least one predefined event, otherwise said area image sensor continues to expose at least one further image frame and to transmit a part of said at least one exposed image frame.

According to an embodiment, said area image sensor and an image data processing device are part of a smart camera. According to an embodiment, said part of the image frame comprises multiple separate sections of said image frame. According to an embodiment, said bigger part of the image frame comprises multiple separate sections of said image frame. According to an embodiment, said bigger part of the image frame is the whole image frame. According to an embodiment, said received part of the image frame determines the size and position of said bigger part of said image frame, or the number of image frames of which said bigger part is transmitted. According to an embodiment, said area image sensor is arranged to expose at least one further image frame and transmitting a part of said at least one further image frame to said image data processing device after said bigger part of at least one further image frame is transmitted to said image data processing device for further analysis. According to an embodiment, said area image sensor is exposing image frames and transmitting parts of image frames without an external trigger signal.

According to a third aspect of the invention, there is provided a computer program product, stored on a computer readable medium and executable in a computing device, wherein the computer program product comprises instructions to expose an image frame of an object to be monitored by an area image sensor, transmit a part of said exposed image frame to an image data processing device, analyse the received part of said image frame by said image data processing device, and further if said received part of said image frame is detected to comprise at least one predefined event, said image data processing device is instructed to transmit a trigger signal for triggering said area image sensor so that said area image sensor transmits a bigger part of at least one further image frame to said image data processing device for further analysis, or if said received part of said image frame is not detected to comprise a predefined event, said area image sensor is instructed to continue exposing at least one further image frame and to transmit a part of said at least one further image frame.

According to an embodiment, said part of the image frame comprises multiple separate sections of said image frame. According to an embodiment, said bigger part of the image frame comprises multiple separate sections of said image frame. According to an embodiment, said bigger part of said image frame is the whole image frame. According to an embodiment, said received part of said image frame determines the size and position of said bigger part of said image frame, or a number of image frames of which a bigger part is transmitted. According to an embodiment, the computer program product further comprises instructions to expose at least one further image frame and to transmit a part of said at least one further image frame to said image data processing device after said bigger part of at least one further image frame is transmitted to said image data processing device for further analysis. According to an embodiment, said area image sensor is exposing image frames and transmitting parts of image frames without an external trigger signal.

DESCRIPTION OF THE DRAWINGS

In the following, the invention will be described in more detail with reference to the appended drawings, in which.

DETAILED DESCRIPTION

Figure 1A:
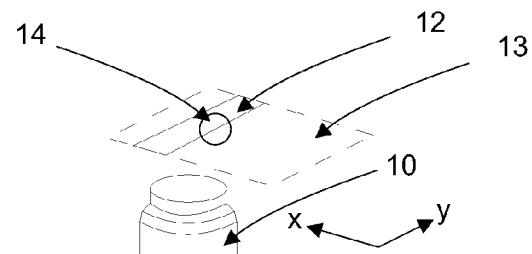
FIGS. 1a-c show inspection states of a machine vision system according to an embodiment of the invention.

Usually, an area image sensor of a machine vision system inspects a moving object and exposes images one image frame, i.e. image matrix at a time as the object being monitored moves past the field of view of the area image sensor. Exposed images are captured images. The object to be monitored may be, for example, the web-like material of a paper or cardboard machine, or some other kind of machine comprising moving parts to be monitored, such as a printing machine comprising a moving roll, or an assembly machine.

Each exposed image is transferred to a processing unit for analysis. The image transferring process from the sensor to the processing unit is time consuming, and thus the larger the size of the images being transferred, the lower the frame frequency of the camera system must be. Because of the limited frame frequency, events that need to be captured completely within a single image may instead end up being captured only partly, for example so that part of the event is in one image and the rest is in the following image. Therefore, machine vision systems are often externally triggered by an external trigger signal received, for example, from a photoelectric cell, automatic logic or pulse sensor, for giving an indication of when images should be exposed so that the whole event is captured within a single image.

However, it is also possible to use area image sensors i.e. image matrix sensors in machine vision systems for the aforementioned usage without external triggering if only a part of the image frame i.e. image matrix is read and transferred to an image data processing device such as to a logic circuit, digital signal processor (DSP) or an image data computer. This read and transferred part of the image frame may be called, for example, a synchronizing image area. When the image data processing device detects a predefined event, such as a definite change, object, or pattern, in the synchronizing image area, the configuration of the image sensor is changed so that the whole image frame, or at least a bigger part of the image frame than the synchronizing image area, is read and transferred from the camera to a memory of the image data processing device for further analysis and/or measuring. The predefined event may be, for example, a hole that is made on purpose to the moving object and/or a deviation such as a definite change, pattern and/or unwanted hole in the object or any other event that is suitable to be monitored by used camera. The predefined event is defined for the image data processing device in advance. Thus, the detected event acts as a trigger for the machine vision system that causes the transmission of the whole, or at least a bigger part of at least one image frame to the image data processing device and for further analysis of the image in the image data processing device. It is also possible, that the size and position of the bigger part of the image frame are dependent on conditions in the synchronizing image area, for example so that the bigger part is aligned to contain the detected event in the middle of the transmitted image area. It is also possible, that the image sensor is not configured to transfer a bigger part of the first image frame after the detected event, but is instead configured to transfer a bigger part of the image frame after, for example, a predetermined number of image frames from the detected event. After transmitting the bigger part of at least one frame, the machine vision system is reconfigured and it resumes reading and transferring only synchronizing image areas until a new predefined event is detected.

In other words, an area image sensor captures images i.e. image frames of a moving object. For capturing an image of the object the image frame area is exposed and exposed image frame area is then captured. In fact capturing includes exposing. After capturing of the image frame area, the area image sensor transmits a part of that image frame to an image data processing device. This transmitted part is so called synchronizing image area part. The image data processing device analyses the synchronizing image area part for detecting a predefined event(s). If the image data processing device detect a predefined event(s) it is arranged to transmit a trigger signal for triggering the area image sensor. On the basis of this trigger signal the area image sensor is reconfigured i.e. configuration of the area image sensor is changed. The area image sensor captures a new image frame essentially from the same area of the object as the image frame comprising the synchronizing image area part comprising the detected predefined event(s).

However, due to reconfiguration, the area image sensor reads a part of the new image frame. This part may be called as a further analysis area part. However, it is also possible that the area image sensor reads more than one parts of the new image frame. In many cases the further analysis area part is bigger than the synchronizing image area part, for example, so that whole predefined event can be seen from the new part if the predefined event was only partly shown in synchronizing image area part. It is also possible that the further analysis area part is smaller or the same size than the synchronizing image area part. The further analysis area part may also have different shape. After reading the further analysis area part, the area image sensor transmits this further analysis area part to the image data processing device for further analysis. After this transmission the area image sensor is again reconfigured and it returns to image and transmit synchronizing image area part(s). However, if the area image sensor does not found any predefined event(s), the area image sensor continues to image and transmit synchronizing image area part(s) to the image data processing device that analyses those parts to find predefined event(s).

A synchronizing image part of the image frame and a further analysis area part of the image frame may comprise multiple separate sections of said image frame i.e. it may consist of several parts. The further analysis area part may also be the whole image frame.

The further analysis area part's size and position relative to the image frame may be determined on the basis of the synchronizing image part comprising at least one predefined event. The synchronizing image part comprising at least one predefined event may also determine a number of image frames that are taken for further analysis.

The area image sensor may capture and transmit synchronizing image parts without an external trigger signal, because the size of the synchronizing image part is predetermined small enough.

Figure 1B:
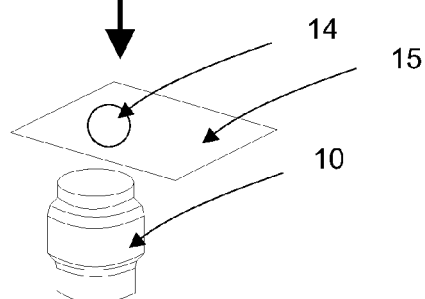
Figure 1C:
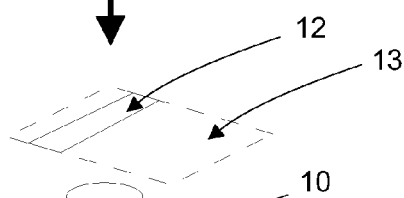

FIGS. 1*a*, 1*b* and 1*c* show inspection states of a machine vision system according to an embodiment of the invention. An area image sensor 10 is arranged to expose images from an object to be monitored 11. In this embodiment the object to be monitored 11 is movable web-like material. FIG. 1*a* shows a first state, a so-called normal state of the machine vision system, where the area image sensor 10 exposes and transfers a synchronizing image area to a memory of an image data processing device (not shown). This synchronizing image area 12 is a part of the image frame 13 i.e. image matrix 13 exposed by the sensor 10 from the object to be monitored 11. The image data processing device is configured to detect events 14 from the synchronizing image area 12. Events 14 to be detected are defined for the processing device in advance. In this embodiment, the event 14 to be detected is a deviation on the moving object to be monitored 11, for example, a hole. If the image data processing device detects at least one event 14 in the synchronizing image area 12, the machine vision system changes to a second state shown in FIG. 1*b*, where the sensor 10 is reconfigured by the image data processing device so that the sensor 10 of the machine vision system reads and transfers a bigger part 15 of at least one image frame 13 to the memory of the image data processing device for more detailed analysis. The bigger part 15 of the image frame 13 is so-called further analysis area. In this embodiment, the bigger part 15 is same as the image frame 13. After transferring the bigger part 15 of at least one image frame 13, the machine vision system resets to the first state and the sensor 10 continues to expose images from the moving object 11 and to read and transfer synchronizing image areas 12 to the image data processing device. If a new event is detected, the image system switches again to the second state.

Figures 2A, 2B:
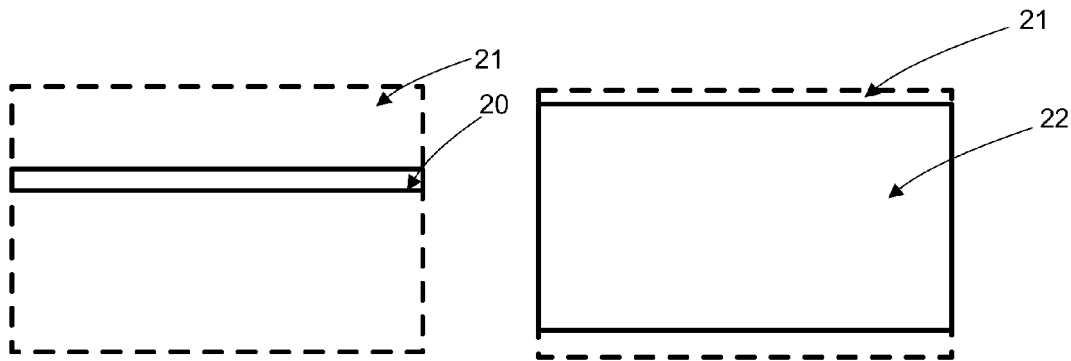
FIGS. 2a-h show sizes of inspection image areas of a machine vision system according to an embodiment of the invention.
Figures 2C, 2D:
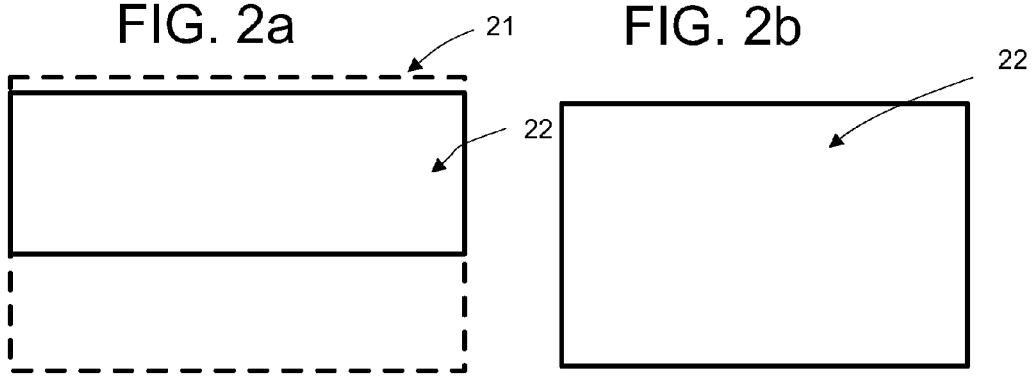
Figures 2E, 2F:
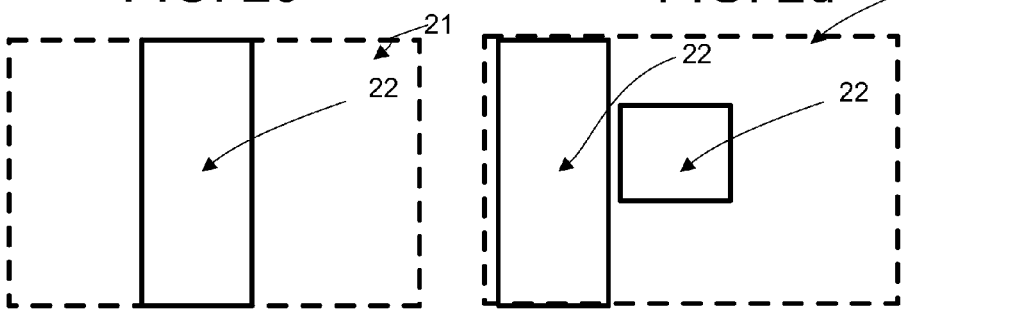
Figures 2G, 2H:
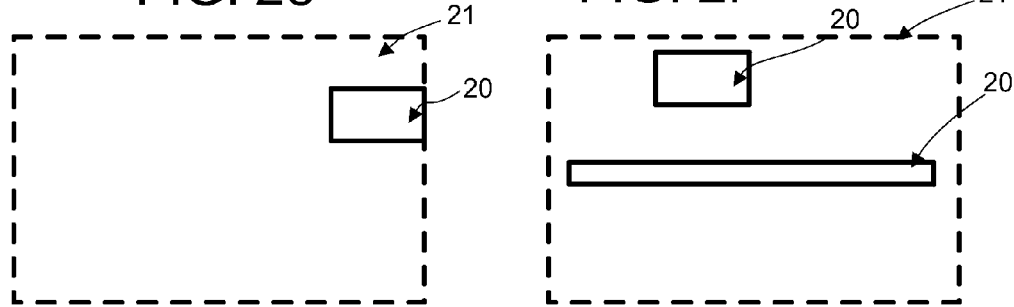

FIG. 2*a* shows a synchronizing image area 20 of an image frame 21 exposed by an area image sensor (not shown) according to an embodiment of the invention. When an image data processing device (not shown) detects a predefined event, for example, a defect in the synchronizing image area 20 i.e. in a part of the exposed image, the sensor is reconfigured to read and transfer a bigger part of at least one image frame i.e. the further analysis area 22 to the image data processing device for further analysis. Some possible areas 22 are also shown in FIGS. 2*b*, 2*c*, 2*d*, 2*e*, 2*f*, 2*g* and 2*h*. In FIG. 2*b*, the area 22 is essentially bigger than synchronizing image area 20, whereas in FIG. 2*c* the area 22 is only slightly bigger than synchronizing image area 20. In FIG. 2*d* the image frame 21 and the further analysis area 22 are the same size. In FIG. 2*e* the further analysis area 22 is orientated differently and in FIG. 2*f* there is two further analysis areas 22. FIG. 2*g* shows a synchronizing image area 20 of an image frame 21 exposed by an area image sensor according to an embodiment of the invention. FIG. 2*h* shows an image frame 21 comprising two synchronizing image areas 20. The number, shape or size of synchronizing image areas 20 in one image frame 21 is not restricted, for example, there could be 1, 2, 3, 4 or even more image areas 20 i.e. separate sections in one image frame 21. In addition, position of synchronizing image area/s 20 in one image frame 21 is not restricted. Further, the number, shape or size of further analysis area 22 is not restricted to shown embodiments, for example, there could be 1, 2, 3, 4 or even more further analysis areas i.e. separate sections that are transmitted to the image data processing device.

In addition, when two or more parts of the exposed image are transmitted to an image data processing device, the image data processing device may define the velocity of the object. And on the base of the defined velocity the image data processing device may, for example, in a trigger signal determine for the area image sensor the size, shape, or position of at least one bigger part of at least one image frame.

Figure 3:
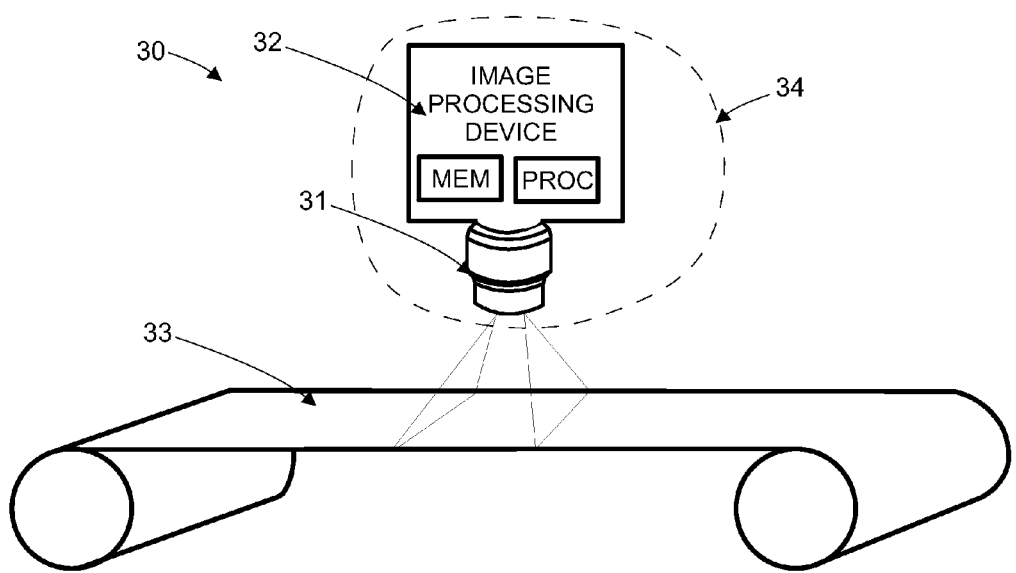
FIG. 3 shows an embodiment of the invention, in which an operating principle of inspection method of a machine vision system is disclosed.

FIG. 3 shows an embodiment of the invention, in which an operating principle of an inspection method of a machine vision system 30 is disclosed in conjunction with a moving object 33. The machine vision system comprises at least one smart camera 34 comprising an area image sensor 31 and an image data processing device part 32. The area image sensor 31 is arranged to expose image frames i.e. image matrixes from the moving object 33 and to transfer a part (i.e. synchronizing image area) of each image frame to the image data processing device part 32 of the smart camera 34.

The image data processing device part 32 comprises at least one processor, at least one memory including computer program code for one or more program units, and means for receiving image data wirelessly or via wired connection, for example, a receiver or a transceiver and means for transferring trigger signals wirelessly or via wired connection, for example, a transmitter or a transceiver. There may be multiple processors e.g. a general purpose processor and a graphics processor and a DSP processor and/or multiple different memories e.g. volatile memory for storing data and programs at run-time and nonvolatile memory like a hard disk for permanently storing data and programs. The image data processing device part 32 of the smart camera 34 may be any computing device suitable for handling image data such as a computer. The image data processing device part 32 is in electronic communication with the area image sensor 31 via signal lines. The smart camera 34 may also include a video controller and an audio controller for generating signals that can be produced to the user with computer accessories. The smart camera 34 produces output to the user through output means. The video controller may be connected to a display. The display may be e.g. a flat panel display or a projector for producing a larger image. The audio controller may be connected to a sound source such as loudspeakers or earphones.

The image data processing device part 32 is configured to receive from the area image sensor 31 a part of the image frame exposed by the area image sensor 31. The image data processing device part 32 analyses the above mentioned image frame part and if the image data processing device part 32 detects a predefined event, it may trigger the area image sensor 31 by indicating that a bigger part or the whole image frame must be transferred to the image data processing device part 32 for further analysis i.e. the image data processing device part 32 requests a larger part of the image frame (further analysis area) from the area image sensor 31. It is also possible that the image data processing device part 32 defines the size of the further analysis area to be transferred or the size may be predefined for the area image sensor 31. In addition, it is possible that the image data processing device part 32 re-configures the area image sensor 31 so that the size and position of the bigger image area are dependent on conditions in the synchronizing image area, for example, so that the detected event is in the middle of the bigger image area i.e. the further analysis area. The number of image frames of which a bigger part is transmitted for further analysis may also be more than one. After the area image sensor 31 has transferred the requested or pre-defined image data, the camera starts to transfer image frame parts until it receives the next trigger signal. The image data processing device part 32 may further be arranged to notify a user of the machine comprising the machine vision system 30.

Figure 4:
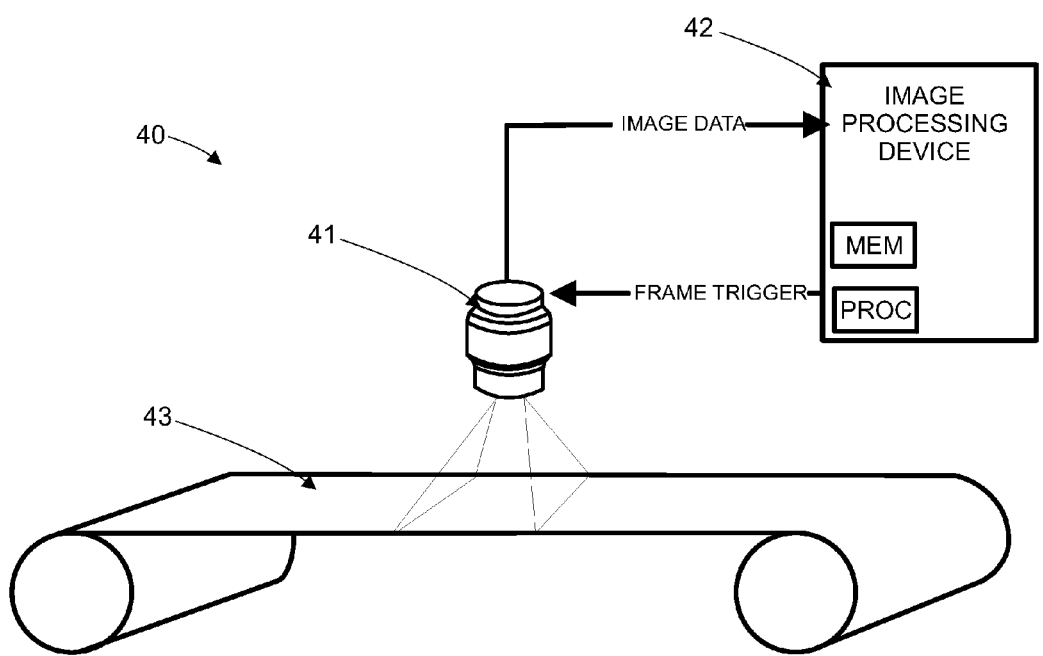
FIG. 4 shows an embodiment of the invention, in which an operating principle of inspection method of a machine vision system is disclosed.

FIG. 4 shows an embodiment of the invention, in which an operating principle of an inspection method of a machine vision system 40 is disclosed in conjunction with a moving object to be monitored 43. The machine vision system comprises at least one area-scan camera (area image sensor) 41 and an image data processing device 42. The area-scan camera 41 is arranged to expose image frames i.e. image matrixes from the object to be monitored 43 and to transfer a part of each image frame to the image data processing device 42.

The image data processing device 42 comprises at least one processor, at least one memory including computer program code for one or more program units, and means for receiving image data wirelessly or via wired connection, for example, a receiver or a transceiver and means for transferring trigger signals wirelessly or via wired connection, for example, a transmitter or a transceiver. There may be multiple processors e.g. a general purpose processor and a graphics processor and a DSP processor and/or multiple different memories e.g. volatile memory for storing data and programs at run-time and nonvolatile memory like a hard disk for permanently storing data and programs. The image data processing device 42 may be any computing device suitable for handling image data such as a computer. The image data processing device 42 is in electronic communication with the camera 41 via signal lines. For handling the signals to/from the signal lines, the image data processing device 42 comprises I/O circuitry. The connection between the camera 41 and the image data processing device 42 is a wired or wireless network. The image data processing device 42 may also include a video controller and an audio controller for generating signals that can be produced to the user with computer accessories. The simulator produces output to the user through output means. The video controller may be connected to a display. The display may be e.g. a flat panel display or a projector for producing a larger image. The audio controller may be connected to a sound source such as loudspeakers or earphones.

The image data processing device 42 is configured to receive from the camera 41 a part of the image data frame exposed by the camera 41. The image data processing device 42 analyses the above mentioned image area part and if the image data processing device 42 detects a predefined event, it forms a trigger signal and transmits it to the camera 41. The trigger signal indicates for the camera 41 that a bigger part or the whole image frame must be transferred to the image data processing device 42 for further analysis i.e. the image data processing device 42 requests a larger part of the image frame from the camera 41 by the trigger signal. It is also possible that the image data processing device 42 defines the size of the area to be transferred in the trigger signal or the size may be predefined for the camera 41. In addition, it is possible that the image data processing device part 42 re-configures the camera 41 so that the size and position of the bigger image area are dependent on conditions in the synchronizing image area, for example so that the detected event is in the middle of the bigger image area i.e. the further analysis area. The number of image frames of which a bigger part is transmitted for further analysis may also be more than one. After the camera 41 has transferred the requested or predefined image data, the camera starts to transfer small image frame parts until it receives the next trigger signal. The image data processing device 42 is further arranged to notify a user of the machine comprising the machine vision system 40.

Some modern cameras also offer the possibility of having multiple predetermined configuration sets, which if used can speed up the process of re-configuring the camera 41 to the different modes. In the case of predetermined configuration sets, instead of a list of parameters, a simple command from the data processing device 42 will be enough to re-configure the camera 41.

Figure 5:
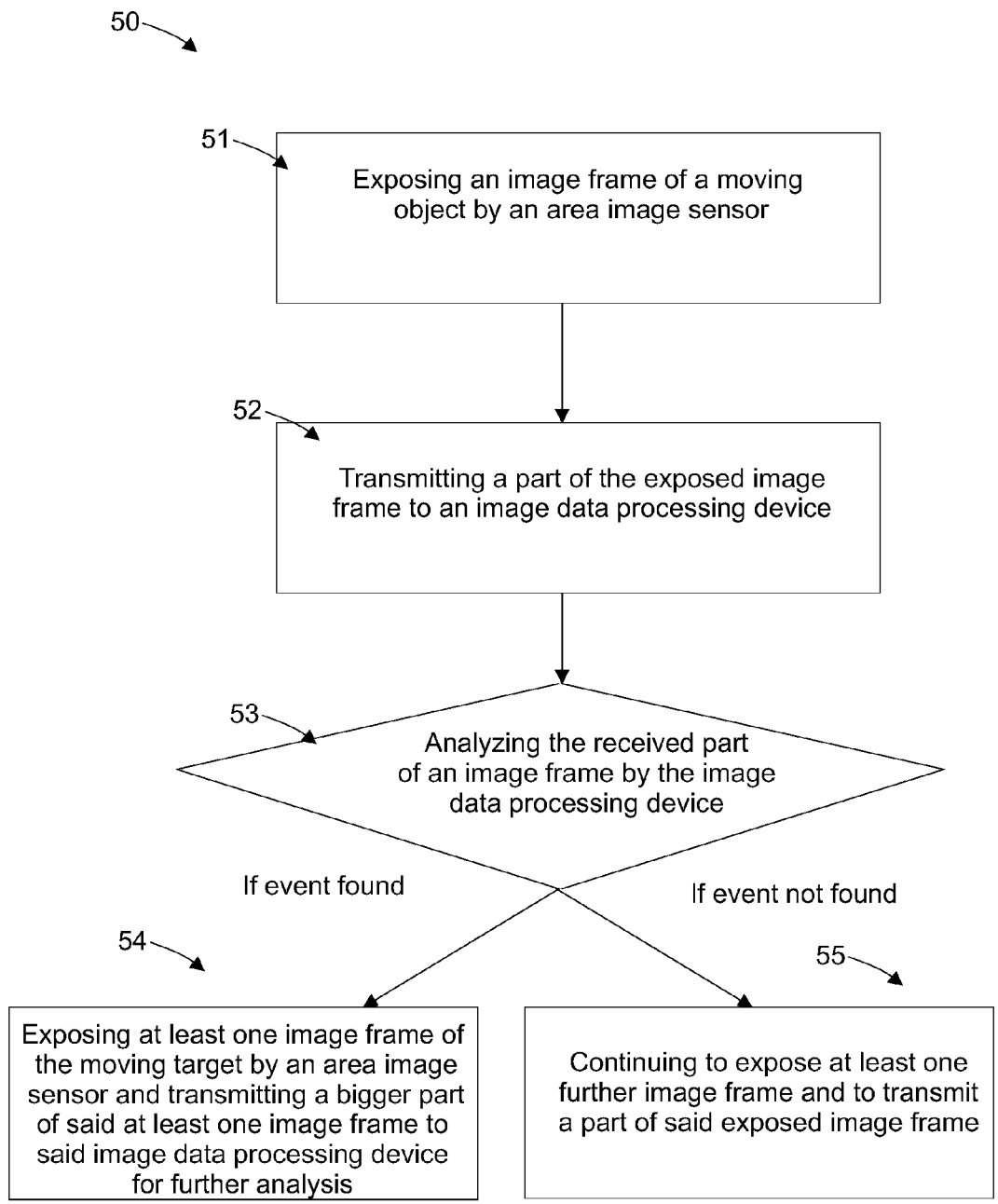
FIG. 5 shows an embodiment of the invention, in which a block diagram of an inspection method of a machine vision system is disclosed.

FIG. 5 shows an embodiment of the invention, in which a block diagram of an inspection method 50 of a machine vision system is disclosed. In step 51 an image frame of a moving object to be monitored is exposed by an area image sensor. In step 52 a part of the exposed image frame is transmitted to an image data processing device. In step 53 the received part of an image frame is analysed by the image data processing device. If the received part of the image frame is detected to comprise a predefined event, in step 54, said area image sensor exposes at least one further image frame of the moving object and transmits a bigger part of said at least one further image frame to said image data processing device for further analysis. If the received part of an image frame is not detected to comprise a predefined event, in step 55, said area image sensor continues to expose at least one further image frame and to transmit a part of said at least one exposed image frame.

In some embodiment of the invention, a part of the image frame that is transmitted to an image data processing device may determine the size and/or position of said bigger part of the image frame, and/or the number of image frames of which a bigger part is transmitted. For example, conditions (size or placement etc.) of a predefined event in the part of the image frame may determine the size and/or position of said bigger part of the image frame, and/or the number of image frames of which a bigger part is transmitted.

In some embodiments of the invention, the image sensor is configured to transfer a bigger part of the first image frame after the detected event, whereas in some embodiments of the invention, the image sensor is configured to transfer a bigger part of the image frame after, for example, a predetermined number of image frames from the detected event.

The various embodiments of the invention can be implemented with the help of computer program code that resides in a memory and causes an apparatus to carry out the invention. For example, the apparatus that is a computing device, for example, an image data processing device may comprise circuitry and electronics for analysing, receiving and transmitting data, a computer program code in a memory, and a processor which, when running the computer program code, causes the apparatus to carry out the features of an embodiment. The processor, when running the computer program code may carry out all the steps of the following method: exposing an image frame of an object to be monitored by an area image sensor, transmitting a part of said exposed image frame, analysing the received part of said image frame, and if said received part of said image frame is detected to comprise at least one predefined event, said image data processing device is arranged to transmit a trigger signal to said area image sensor, and wherein said area image sensor is arranged to transmit a bigger part of said image frame to said image data processing device for further analysis, or if said received part of said image frame is not detected to comprise a predefined event, said area image sensor continues to expose at least one further image frame and to transmit a part of said at least one further image frame.

Considerable advantages are achieved by the present invention when compared to methods and systems of existing machine vision systems comprising at least one area-scan camera. By means of the arrangement according to the invention it is possible to use area-scan cameras without a need of an external trigger signal. In addition, by means of the arrangement according to the invention it is also possible to utilize the data of the whole image frame whenever needed. The present invention is not limited to the above-presented embodiments, but it can be modified within the scope of the appended claims.

It is obvious that the present invention is not limited solely to the above-presented embodiments, but it can be modified within the scope of the appended claims.

The invention claimed is:

1. A one camera fault detection method, comprising:
exposing an image frame of an to be monitored by an area image sensor;
wherein the method further comprises;
transmitting an image part of said image frame of the object to be monitored to an image data processing device;
analysing said image part of said image frame of the object to be monitored by said image data processing device, wherein;
if said image part of said image frame of the object to be monitored is detected to comprise at least one predefined event, said image data processing device is arranged to transmit a trigger signal for triggering said area image sensor so that said area image sensor is reconfigured to expose a further image frame of said at least one predefined event and to transmit an image part of said further image frame of said at least one predefined event to said image data processing device for further analysis, wherein conditions in said image part of said image frame of the object to be monitored determines the size and position of said image part of said further image frame of said at least one predefined event to be transmitted, and
if said image part of said image frame of the object to be monitored is not detected to comprise a predefined event, said area image sensor continues back to expose an image frame of the object to be monitored and to transmit an image part of said image frame of the object to be monitored to the image data processing device.

2. The method according to claim 1, wherein said image part of said image frame of the object to be monitored comprises multiple separate sections.

3. The method according to claim 1, wherein said image part of said further image frame of said at least one predefined event comprises multiple separate sections.

4. The method according to claim 1, wherein said image part of said further image frame of said at least one predefined event is the whole further image frame.

5. The method according to claim 1, wherein said image part of said image frame of the object to be monitored comprising at least one predefined event determines a number of further image frames of said at least one predefined event.

6. The method according to claim 1, wherein said area image sensor is arranged to expose an image frame of the object to be monitored and transmit an image part of said image frames of the object to be monitored without an external trigger signal.

7. A machine vision system for an object to be monitored using one camera and comprising an area image sensor and an image data processing device wherein said area image sensor is arranged to expose an image frame of said object to be monitored and to transmit an part of the image frame of the object to be monitored to said image data processing device for analysing;
if said first image part of said image frame of the object to be monitored is detected to comprise at least one predefined event, said image data processing device is arranged to transmit a trigger signal for triggering said area image sensor so that said area image sensor is reconfigured to expose a further image frame of said at least one predefined event and to transmit an image part of said further image frame of said at least one predefined event to said image data processing device for further analysis, wherein conditions in said image part of said image frame of the object to be monitored determines the size and position of said image part of said further image frame of said at least one predefined event to be transmitted, and
if said image part of said image frame of the object to be monitored is not detected to comprise a predefined event, said area image sensor continues back to expose an image frame of the object to be monitored and to transmit an image part of said-exposed image frames of the object to be monitored to the image data processing device.

8. The machine vision system according to claim 7, wherein said area image sensor and an image data processing device are part of a smart camera.

9. The machine vision system according to claim 7, wherein said image part of the object to be monitored comprises multiple separate sections.

10. The machine vision system according to claim 7, wherein said image part of said further image frame of said at least one predefined event comprises multiple separate sections.

11. The machine vision system according to claim 7, wherein said image part of said further image frame of said at least one predefined event is the whole image frame.

12. The machine vision system according to claim 7, wherein said image part of said image frame of the object to be monitored comprising at least one predefined event determines a number of further image frames of said at least one predefined event.

13. The machine vision system according to claim 7, wherein said area image sensor is arranged to expose an image frame of the object to be monitored and to transmit an image part of said image frame of the object to be monitored to said image data processing device after said image part of said further image frame of said at least one predefined event is transmitted to said image data processing device for further analysis.

14. The machine vision system according to claim 7, wherein said area image sensor is arranged to expose an image frames of the object to be monitored and to transmit an image part of said image frame of the object to be monitored without an external trigger signal.

15. A computer program product, stored on a non-transitory computer readable medium and being executable in a computing device, wherein the computer program product comprises instructions to:
expose an image frame of an object to be monitored by an area image sensor;
wherein the computer program product further comprises instructions to;
transmit an image part of said image frame of the object to be monitored to an image data processing device;
analyse said image part of said image frame of the object to be monitored by said image data processing device, wherein;
if said image part of said image frame of the object to be monitored is detected to comprise at least one predefined event, said image data processing device is instructed to transmit a trigger signal for triggering said area image sensor so that said area image sensor is reconfigured to expose a further image frame of said at least one predefined event and to transmit an image part of said further image frame of said at least one predefined event to said image data processing device for further analysis, wherein conditions in said image part of said image frame of the object to be monitored determines the size and position of said image part of said further image frame of said at least one predefined event to be transmitted, and
if said image part of said image frame of the object to be monitored is not detected to comprise a predefined event, said area image sensor is instructed to expose an image frames of the object to be monitored and to transmit an image part of said image frame of the object to be monitored to the image data processing device.

16. The computer program product according to claim 15, wherein said image part of the object to be monitored comprises multiple separate sections.

17. The computer program product according to claim 15, wherein said image part of said further image frame of said at least one predefined event comprises multiple separate sections or wherein said image part of said further image frame of said at least one predefined event is the whole image frame.

18. The computer program product according to claim 15, wherein said image part of said image frame of the object to be monitored comprising at least one predefined event determines a number of further image of said at least one predefined event.

19. The computer program product according to claim 15, wherein the computer program product further comprises instructions to:
expose an image frame and transmitting an image part of said image frame of the object to be monitored to said image data processing device after said image part of said further image frame of said at least one predefined event is transmitted to said image data processing device for further analysis.

* * * * *